United States Patent
Yamaya et al.

(10) Patent No.: US 9,510,797 B2
(45) Date of Patent: Dec. 6, 2016

(54) INTEGRATED PET/MRI SCANNER

(75) Inventors: Taiga Yamaya, Chiba (JP); Fumihiko Nishikido, Chiba (JP); Takayuki Obata, Chiba (JP); Mikio Suga, Chiba (JP); Kazuyuki Saito, Chiba (JP); Mitsuo Watanabe, Hamamatsu (JP); Eiichi Tanaka, Hamamatsu (JP)

(73) Assignees: NATIONAL INSTITUTE OF RADIOLOGICAL SICENCES, Chiba (JP); HAMAMATSU PHOTONICS K.K., Shizuoka (JP)

( * ) Notice: Subject to any disclaimer, the term of this patent is extended or adjusted under 35 U.S.C. 154(b) by 452 days.

(21) Appl. No.: 13/880,842

(22) PCT Filed: Oct. 25, 2010

(86) PCT No.: PCT/JP2010/068810
§ 371 (c)(1),
(2), (4) Date: Apr. 22, 2013

(87) PCT Pub. No.: WO2012/056504
PCT Pub. Date: May 3, 2012

(65) Prior Publication Data
US 2013/0211233 A1   Aug. 15, 2013

(51) Int. Cl.
*A61B 6/00* (2006.01)
*A61B 5/055* (2006.01)
(Continued)

(52) U.S. Cl.
CPC ........... *A61B 6/4417* (2013.01); *A61B 5/0035* (2013.01); *A61B 5/055* (2013.01);
(Continued)

(58) Field of Classification Search
CPC .... A61B 5/055; A61B 6/037; A61B 6/4258; A61B 6/4417; A61B 5/0035; A61B 6/5247; A61B 6/501; G01T 1/1603; G01R 33/481; G01R 33/34076
See application file for complete search history.

(56) References Cited

U.S. PATENT DOCUMENTS 7,626,392 B2   12/2009  Nistler et al.
2003/0020475 A1  1/2003  Leussler
(Continued)

FOREIGN PATENT DOCUMENTS

JP   A-2003-38459    2/2003
JP   A-2006-500082   1/2006
(Continued)

OTHER PUBLICATIONS

Wikipedia, "Magnetic resonance imaging", archived Oct. 22, 2009, retrieved Mar. 22, 2015.*
(Continued)

*Primary Examiner* — Katherine Fernandez
*Assistant Examiner* — Colin T Sakamoto
(74) *Attorney, Agent, or Firm* — Oliff PLC

(57) ABSTRACT

In the integrated PET/MRI scanner provided with an RF coil for MRI and a plurality of PET detectors in the measuring port of the MRI scanner, the PET detectors are disposed with spaces therebetween and at least the transmitting coil elements of the RF coil for MRI are disposed between adjacent PET detectors. Here, the PET detectors are disposed in the circumferential direction of the measuring port with spaces therebetween and the transmitting coil elements are disposed in the axial direction of the measuring port. Alternatively, at least some of the PET detectors are disposed in the axial direction of the measuring port with spaces therebetween and the transmitting coil elements are disposed between adjacent PET detectors. The PET detectors can be DOI-type detectors capable of detecting position in the depth direction.

5 Claims, 19 Drawing Sheets

(51) Int. Cl.
*A61B 6/03* (2006.01)
*G01T 1/16* (2006.01)
*G01R 33/48* (2006.01)
*A61B 5/00* (2006.01)
*G01R 33/34* (2006.01)

(52) U.S. Cl.
CPC ............ *A61B 6/037* (2013.01); *A61B 6/4258* (2013.01); *A61B 6/501* (2013.01); *A61B 6/5247* (2013.01); *G01R 33/481* (2013.01); *G01T 1/1603* (2013.01); *G01R 33/34076* (2013.01)

(56) References Cited

U.S. PATENT DOCUMENTS

| | | | |
|---|---|---|---|
| 2003/0193380 | A1 | 10/2003 | De Swiet et al. |
| 2006/0250133 | A1 | 11/2006 | Krieg et al. |
| 2007/0055127 | A1* | 3/2007 | Ladebeck et al. ............ 600/407 |
| 2008/0284428 | A1 | 11/2008 | Fiedler et al. |
| 2008/0287772 | A1 | 11/2008 | Declerck et al. |
| 2009/0105583 | A1 | 4/2009 | Martin et al. |
| 2009/0108206 | A1 | 4/2009 | Breuer et al. |
| 2009/0270718 | A1* | 10/2009 | Peter et al. ................... 600/411 |
| 2010/0102813 | A1 | 4/2010 | Schulz et al. |
| 2012/0136237 | A1 | 5/2012 | Benlloch Baviera et al. |

FOREIGN PATENT DOCUMENTS

| | | |
|---|---|---|
| JP | A-2006-280929 | 10/2006 |
| JP | A-2008-48923 | 3/2008 |
| JP | A-2008-536600 | 9/2008 |
| JP | A-2009-75108 | 4/2009 |
| JP | A-2009-121929 | 6/2009 |
| JP | A-2009-270971 | 11/2009 |
| JP | A-2010-515517 | 5/2010 |
| JP | A-2010-160045 | 7/2010 |
| WO | WO 2010/079251 A1 | 7/2010 |

OTHER PUBLICATIONS

Ledden et al., "A volume coil transmit, surface coil receive system for brain imaging at 3T", Proceedings of the 7th Annual Meeting of ISMRM, Philadelphia, 1999. p. 168.*

Catana et al., "Simultaneous Acquisition of Multislice PET and MR Images: Initial Results with a MR-Compatible PET Scanner," *The Journal of Nuclear Medicine*, Dec. 2006, vol. 47, No. 12, pp. 1968-1976.

Schlyer et al., "A Simultaneous PET/MRI Scanner Based on RatCAP in Small Animals," *IEEE Nuclear Science Symposium Conference Record*, 2007, vol. 5, pp. 3256-3259.

Schlemmer et al., "Simultaneous MR/PET Imaging of the Human Brain: Feasibility Study," *Radiology*, Sep. 2008, vol. 248, No. 3, pp. 1028-1035.

Judenhofer et al., "Simultaneous PET-MRI: A New Approach for Functional and Morphological Imaging," *Nature Medicine*, Apr. 2008, vol. 14, No. 4, pp. 459-465.

Peng et al., "Placing a PET Insert in the Bore of a 7T Magnet: Initial Study of the Interactions of the MRI System with the PET Shielding," *Proc. Intl. Soc. Mag. Reson. Med.*, 2006, vol. 14, p. 1358.

International Search Report issued in International Patent Application No. PCT/JP2010/068810 dated Nov. 16, 2010.

Jul. 15, 2014 Office Action issued in Japanese Application No. 2012-540549 (with translation).

International Preliminary Report on Patentability issued in International Application No. PCT/JP2010/068810 on Apr. 30, 2013 (with translation).

* cited by examiner

INTEGRATED PET/MRI SCANNER

TECHNICAL FIELD

The present invention relates to an integrated PET/MRI scanner that integrates a PET (Positron Emission Tomography) scanner and an MRI (Magnetic Resonance Imaging) scanner, and more particularly to an integrated PET/MRI scanner in which PET detectors can be placed close to a measuring object to increase the sensitivity and spatial resolution of PET.

BACKGROUND ART

PET is a method of administering a compound that is labeled with positron-emitting radionuclides and imaging the distribution of the compound in the body as a tomographic image by processing data obtained by PET detectors including combinations of light receiving elements and scintillators, or CdTe, CZT, or other semiconductor detectors. While X-ray CT (Computed Tomography) and MRI based tomographic images provide anatomical information, PET images are referred to as functional images which express biological functional information. For example, PET images are capable of highly sensitive tumor detection though not precise in position. To add accurate positional information to a PET image, an X-ray CT image or MRI image which can provide exact positional information needs to be superposed on the PET image. For higher superposition accuracy and efficient scanning, PET/CT scanners that combine a PET scanner with an X-ray CT scanner have been prevalent. However, since X-ray CT typically has an exposure level several times higher than that of PET, CT exposure is not negligible.

Instead of the CT scanner, MRI scanners capable of acquiring anatomical images without radiation exposure are receiving attention. PET/MRI scanners that can simultaneously acquire a PET image and an MRI image have been under research and development (see Patent Literature 1 and Non-Patent Literature 1).

PET detectors are composed of scintillators which emit light in response to incident of annihilation radiation and light receiving elements which detect the emitted light. In past approaches, the scintillation light has been brought out to a location less affected by a magnetic field through optical fibers or the like before received by the light receiving elements. Such approaches deteriorate the PET performance because of attenuation of the scintillation light. A semiconductor light receiving element method has recently been developed in which, as shown in FIG. 1, all the detector units (hereinafter, referred to as PET detectors) 10 of the PET scanner are arranged within the static magnetic field of the MRI scanner 8, using APDs (Avalanche Photodiodes) or Geiger-mode APDs (also referred to as SiPMs) less susceptible to a magnetic field as the light receiving elements. Small animal PET scanners and head PET scanners have actually been developed (see Non-Patent Literatures 2 to 4 and Patent Literatures 2 to 4).

CITATION LIST

Patent Literature

Patent Literature 1: Japanese Patent Application Laid-Open No. 2008-48923
Patent Literature 2: U.S. Pat. No. 7,626,392 B2
Patent Literature 3: U.S. Patent Application Laid-Open Publication No. 2008/0287772 A1
Patent Literature 4: U.S. Patent Application Laid-Open Publication No. 2009/0108206 A1
Patent Literature 5: Japanese Patent Application Laid-Open No. 2009-121929
Patent Literature 6: Japanese Patent Application Laid-Open No. 2009-270971

Non-Patent Literature

Non-Patent Literature 1: Ciprian Catana et al. "Simultaneous Acquisition of Multislice PET and MR images: Initial Results with a MR-Compatible PET Scanner" The Journal of Nuclear Medicine, Vol. 47, No. 12, December 2006, pp. 1968-1976
Non-Patent Literature 2: Schlyer D, et al., "A Simultaneous PET/MRI scanner based on RatCAP in small animals," IEEE Nuclear Science Symposium Conference Record, Volume: 5, pp: 3256-3259, 2007
Non-Patent Literature 3: Schlemmer H W, et al. Simultaneous MR/PET Imaging of the Human Brain: Feasibility Study. Radiology, 2008:248, 1028-1035.
Non-Patent Literature 4: Judenhofer M S, et al, Simultaneous PET-MRI: a new approach for functional and morphological imaging. Net Med 2008; 14(4): 459-65.

SUMMARY OF THE INVENTION

Problem to be Solved by the Invention

In general, the PET sensitivity increases as the scintillators of the PET detectors are placed closer to the measuring object. A deterioration of resolution due to angular deviation, which is a deviation of a pair of annihilation radiations emitted in opposite directions from a positron-emitting radionuclide in the measuring object from a 180° direction, can also be suppressed. However, in the conventional integrated PET/MRI scanners, as shown in FIG. 1, the PET detectors 10 arranged in the measuring port 8P of the MRI scanner 8 have been located outside a transmitting and receiving RF coil 42 so that the PET detectors 10 will not affect MRI measurement. There are a type of transmitting and receiving RF coil 42 in which transmitting coil elements are arranged separately from receiving coil elements, and a type in which the same coil elements are used for both transmission and reception. At least the transmitting coil elements need to be located away from the measuring object for the purpose of uniform excitation. Consequently, the PET detectors 10 have a limit to being placed closer to the measuring object, with the problems that the PET sensitivity cannot be increased and that the deterioration of resolution due to angular deviations cannot be suppressed.

The present invention has been achieved in order to solve the foregoing conventional problems, and it is an object thereof to provide an integrated PET/MRI scanner in which PET detectors can be placed close to a measuring object to increase the sensitivity and spatial resolution of PET.

Means for Solving the Problem

The foregoing object of the present invention has been achieved by the provision of an integrated PET/MRI scanner including an RF coil for MRI and a plurality of PET detectors in a measuring port of an MRI scanner, wherein the PET detectors are disposed with spaces therebetween and at least a transmitting coil element of the RF coil for MRI is disposed between adjacent PET detectors.

The PET detectors may be disposed with spaces in a circumferential direction of the measuring port. The transmitting coil element may be disposed in an axis direction of the measuring port.

Alternatively, at least part of the PET detectors may be disposed with a space in the axial direction of the measuring port. The transmitting coil element may be disposed between adjacent PET detectors.

A plurality of detector rings each including a ring-like arrangement of the PET detectors may be disposed with spaces therebetween. The transmitting coil element may be disposed between adjacent detector rings.

An end of a receiving coil element of the RF coil for MRI on an inner side of the measuring port may be located further in the measuring port than an end of the PET detectors on the inner side of the measuring port.

An end of the transmitting coil element on the inner side of the measuring port may be located further in the measuring port than an end of a radio wave shield on the inner side of the measuring port, the radio wave shield being formed on the PET detector.

The PET detector may include a semiconductor detector that senses radiation and converts the radiation into an electrical signal.

Alternatively, the PET detector may include a combination of a scintillator that senses radiation and emits light and a light receiving element that senses the light emitted from the scintillator and converts the light into an electrical signal. The scintillator may be located further in the measuring port than the light receiving element.

The entire PET detectors may be covered with a radio wave shield.

An outer periphery of the scintillator of the PET detector may have no radio wave shield to cover the scintillator. The radio wave shield may be disposed between the scintillator and the light receiving element.

An end of the scintillator of the PET detector on the inner side of the measuring port may be located further in the measuring port than the end of the transmitting coil element on the inner side of the measuring port.

The radio wave shield may be shaped like a wire mesh.

The radio wave shield may be shaped like a grid plate having an opening corresponding to a light receiving surface of the light receiving element.

The grid platelike radio wave shield may also serve as a reflector.

The radio wave shield may be disposed to avoid the light receiving surface of the light receiving element of the PET detector.

The radio wave shield may be shaped like a grid line arranged between light receiving elements of an array light receiving element of the PET detector.

The transmitting coil element may be shaped like a plate and disposed to be wide in a radial direction as viewed from a center of the measuring port.

A light guide may be arranged between the scintillator and the light receiving element of the PET detector.

The light guide may include the radio wave shield.

The PET detector may be a DOI-type detector capable of detecting position in a depth direction.

The PET detectors may be movable in the axial direction of the measuring port.

Advantageous Effects of Invention

According to the present invention, at least transmitting coil elements are disposed between PET detectors. The scintillators of the PET detectors can thus be placed closer to the measuring object without being interfered with the transmitting coil elements which are preferably located away from the measuring object. Thus, the PET sensitivity can be improved without sacrificing the MRI performance.

In particular, suppose that the PET detectors are composed of a combination of a scintillator that senses radiation and emits light and a light receiving element that senses the light emitted from the scintillator and converts the light into an electrical signal, and the scintillators are located further in the measuring port than the light receiving elements. In such a case, a radio wave shield for allowing the use of the PET detector in the measuring port of the MRI scanner is disposed between the scintillator and the light receiving element except for the outer periphery of the scintillator. The radio wave shields are located further in the measuring port than the ends of the transmitting coil elements of the RF coil for MRI on the inner side of the measuring port. The ends of the scintillators on the inner side of the measuring port are protruded further into the measuring port than the transmitting coils as far as not beyond receiving coils. Consequently, the scintillators can be placed as close to the measuring object as possible to reduce gaps between the PET detectors accordingly, with a further improvement in sensitivity without affecting MRI.

Moreover, DOI (Depth of Interaction) type detectors (see Patent Literatures 5 and 6) capable of detecting position in a depth direction can be used as the PET detectors for even higher resolution.

DESCRIPTION OF EMBODIMENTS

Hereinafter, embodiments of the present invention will be described in detail with reference to the drawings.

Figure 1:
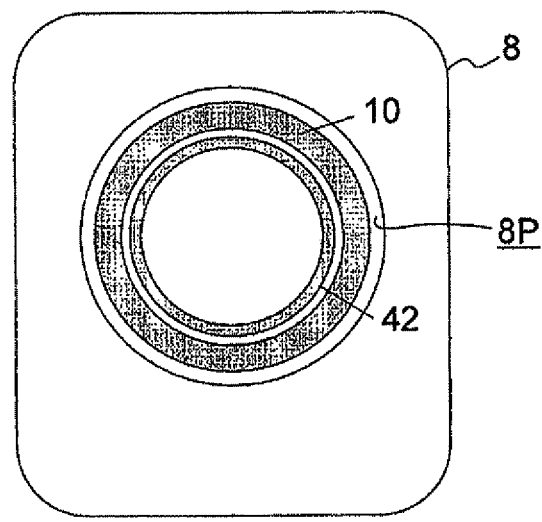
FIG. 1 is a front view showing the overall configuration of an example of a conventional integrated PET/MRI scanner.
Figure 2:
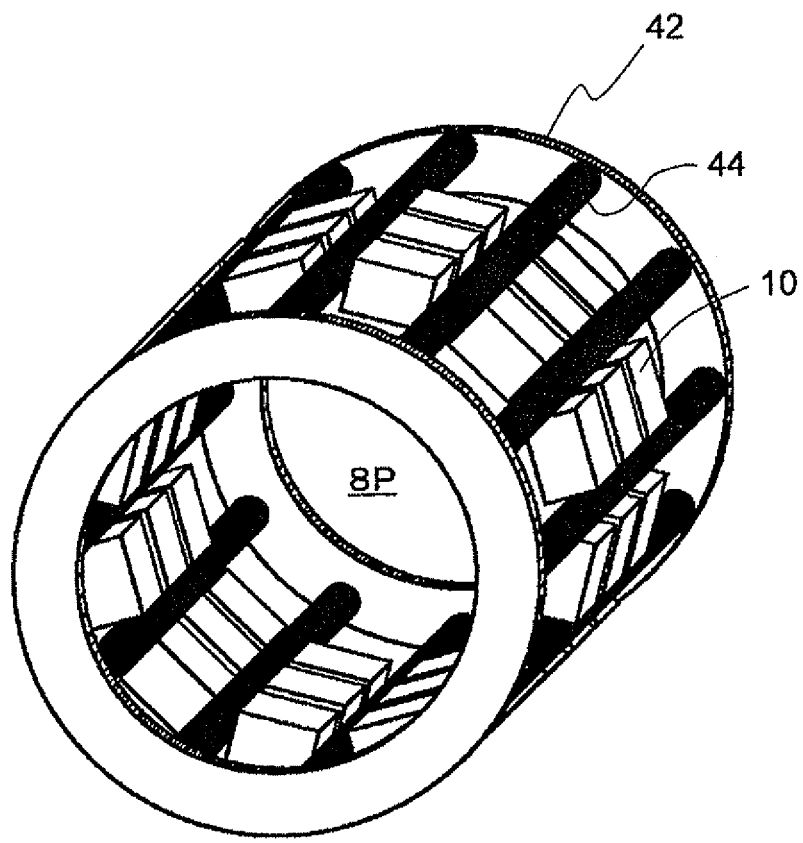
FIG. 2 is a perspective view showing an arrangement of PET detectors and an RF coil according to a first embodiment of the present invention.

As shown in FIG. 2 (a perspective view showing the configuration of essential parts) and FIG. 3 (transverse cross-sectional view), a first embodiment of the present invention is a transmitting and receiving RF coil (hereinafter, also referred to simply as an RF coil) 42 of so-called birdcage type for head MRI examination. Transmitting and receiving coil elements (hereinafter, also referred to simply as coil elements) 44 contained in bar-shaped cases extending in the axial direction of a measuring port 8P are arranged in parallel, with spaces therebetween. A large number of PET detectors 10 are disposed with spaces therebetween in the circumferential direction of the measuring port 8P. The respective transmitting and receiving coil elements 44 are configured to be contained in the spaces between the PET detectors 10.

Figure 3:
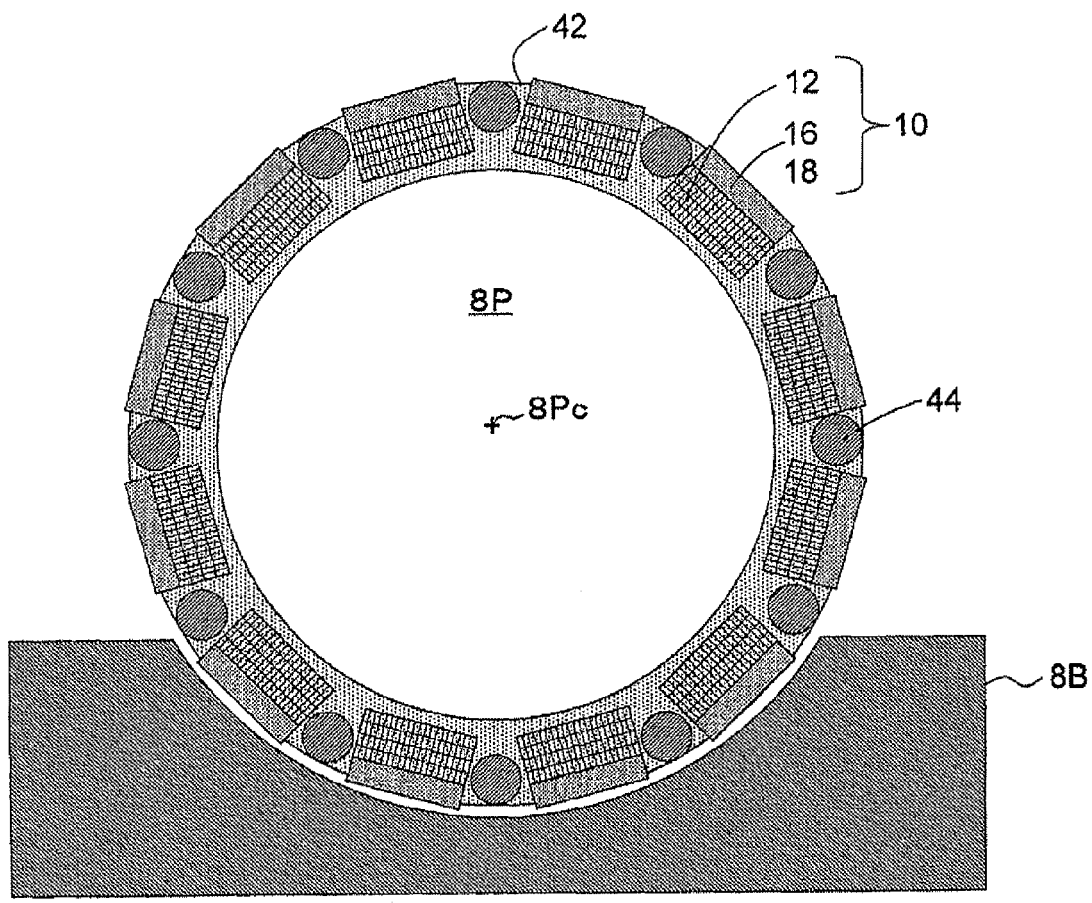
FIG. 3 is a transverse cross-sectional view of the first embodiment seen from the front.

As shown in FIG. 3, the PET detectors 10 are composed of a combination of a light receiving element 16 and a scintillator 12. The scintillator 12 is located further in the measuring port than the light receiving element 16. The PET detectors 10 are DOI-type detectors in which the scintillator 12 is divided into four stages in the depth direction (radial direction as viewed from the center 8Pc of the measuring port). However, the PET detectors 10 need not necessarily be limited to four stages. PET detectors of non-DOI type (i.e., the number of stages is one) may be used. The scintillator 12 need not necessarily be a scintillator block (array type) including a combination of assemblies of sub-divided small scintillators, and may be a single scintillator (integral type) that includes no optical discontinuity point or optical discontinuity plane. In general, the resolution of a DOI-type detector can be increased as the number of stages increases. CdTe, CZT, or other semiconductor detectors may be used instead of the scintillation detectors composed of a combination of a light receiving element and a scintillator. While the RF coil is of commonly-used birdcage type, other RF coils having similar shapes may be used.

The measuring object is not limited to a human head.

In FIG. 3, 8B represents the base of an MRI scanner 8, or a bed on which the measuring object is placed, for example.

Figure 4:
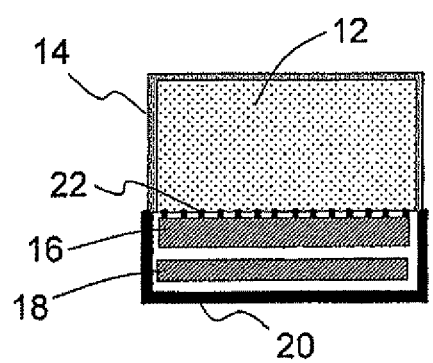
FIG. 4 is a longitudinal cross-sectional view showing the configuration of the PET detectors used in the first embodiment.
Figure 5:
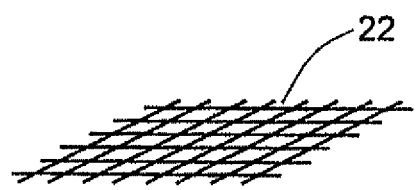
FIG. 5 is a perspective view showing a wire mesh-like radio wave shield used in the PET detector shown in FIG. 4.

As shown in detail in FIG. 4, the PET detector 10 includes: the scintillator 12; a light shielding member 14 which covers the outer periphery of the scintillator 12, is made of a nonmagnetic and insulating body, will not shield radio waves, and also serves as a casing; the light receiving element 16 which receives light emitted from the scintillator 12; a front end circuit 18 for performing amplification, calculation, and other processing on an output of the light receiving element 16; a radio wave shield 20 which shields the portions of the light receiving element 16 and the front end circuit 18 to allow use in an MRI magnetic field; and a wire mesh-like radio wave shield 22 like shown in FIG. 5, which is disposed between the scintillator 12 and the light receiving element 16, shields radio waves, and sufficiently transmits scintillation light. The ends of the coil elements 44 of the RF coil 42 on the inner side of the measuring port 8P (ends directed toward the center 8Pc of the measuring port) are preferably located further in the measuring port 8P than the ends of the radio wave shields 22 on the inner side of the measuring port 8P.

To guide as much scintillation light into the light receiving element 16 as possible, the light shielding member 14 may be made of a material that also has the function of a reflector. A reflector may be interposed between the light shielding member 14 and the scintillator 12. Such reflectors also need to be a nonmagnetic and insulating body.

Figure 6:
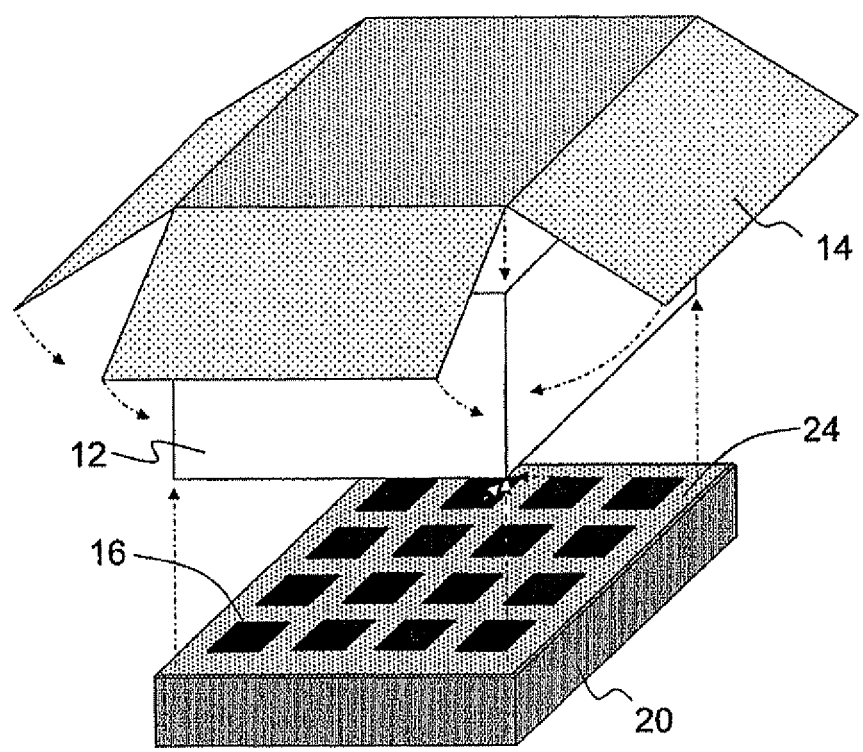
FIG. 6 is an exploded perspective view showing a detailed configuration of a scintillator portion of the same.

The scintillator 12 may be of array type or integral type. As shown in FIG. 6, the outer periphery of the scintillator 12 not in contact with light receiving elements 16 is covered with the light shielding member 14. The scintillator 12 and the light receiving elements 16 are optically coupled by grease or the like, for example. The radio wave shield 20 is made of copper foil, for example, and is grounded.

The wire mesh-like radio wave shield 22 may be a copper mesh, for example.

Figure 7:
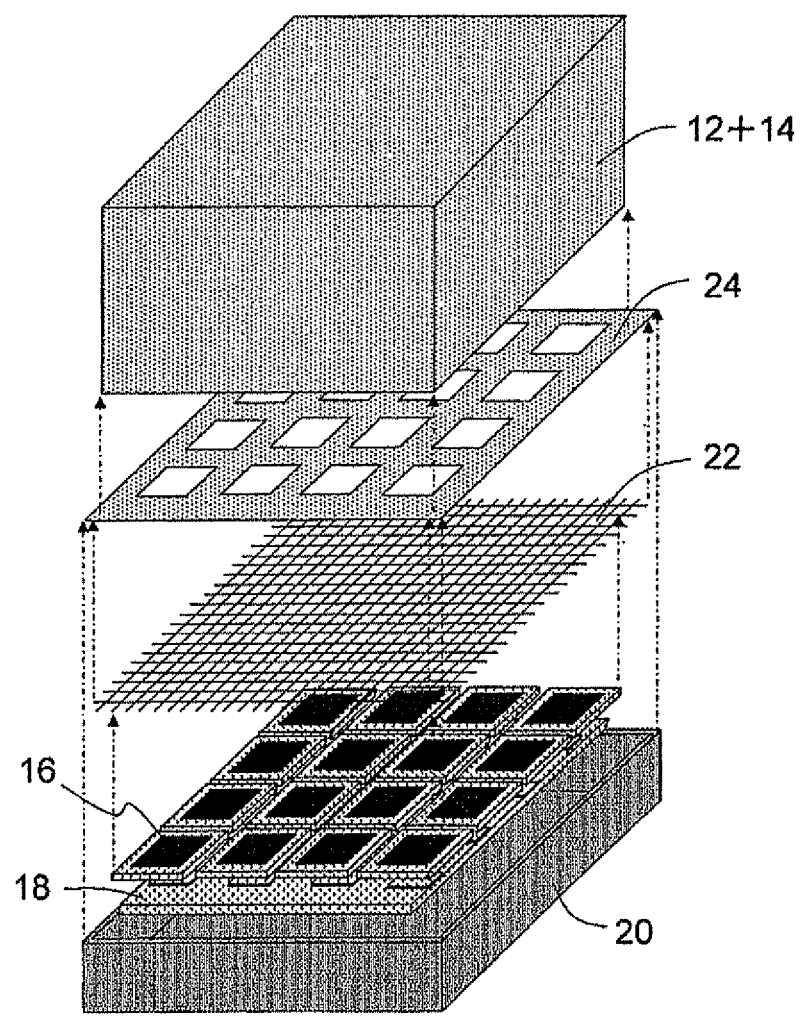
FIG. 7 is an exploded perspective view showing a detailed configuration of a light receiving element portion of the same.

As shown in FIGS. 6 and 7, a reflector 24 intended to fill the gaps between the light receiving surfaces to avoid waste of light for improving light receiving efficiency is disposed between the light receiving elements 16 and the scintillator 12. Examples of the reflector 24 include a thin sheet of multi-polymer mirror and white powder. The reflector 24 may be omitted.

In the present embodiment, no radio wave shield for covering the scintillator 12 is arranged on the outer periphery of the scintillator 12. Radio wave shielding is provided between the scintillator 12 and the light receiving elements 16, or around the portions of the light receiving elements 16 and the front end circuit 18 in particular. This prevents radio wave shielding from lying on the inner side of the coil elements 44 to lower the MRI sensitivity. Since the scintillator portions on the inner side of the measuring port are protruded further in the measuring port than the coil elements 44, the PET detectors are expected to have accordingly high sensitivity.

Figure 8:
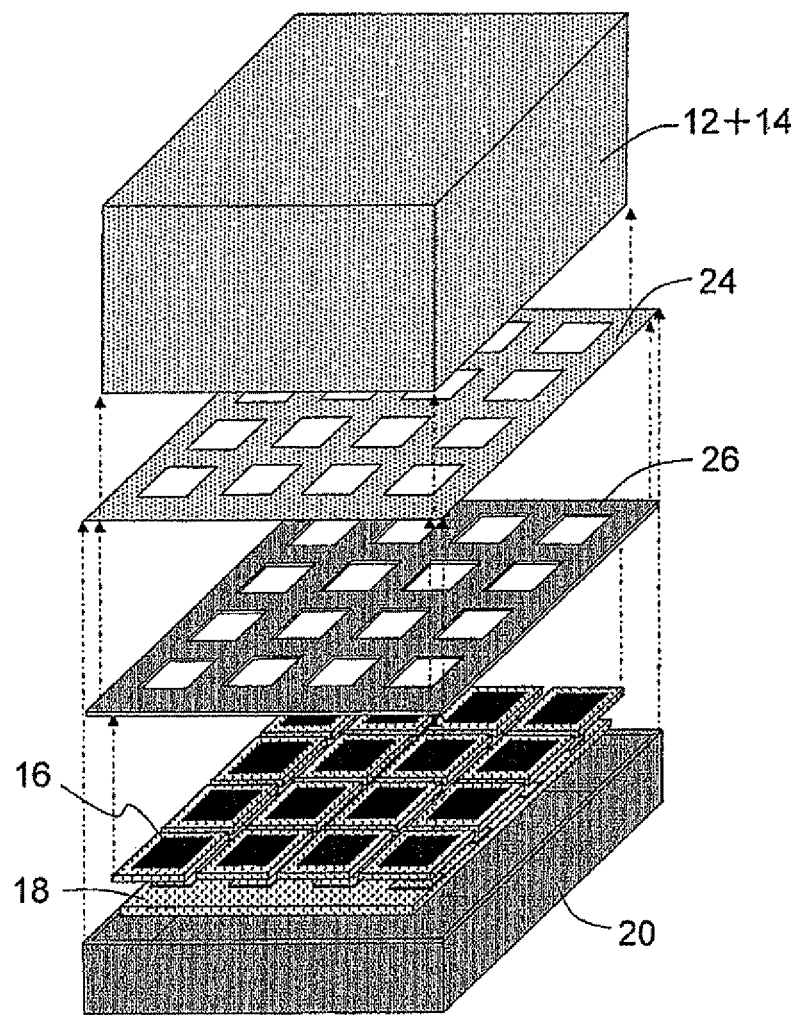
FIG. 8 is an exploded perspective view showing the configuration of a modification of the PET detector.

In the PET detector shown in FIGS. 4 to 7, the wire mesh-like radio wave shield 22 is used as the radio wave shield between the scintillator 12 and the light receiving elements 16. However, as in a modification shown in FIG. 8, a grid plate-like radio wave shield 26 having openings corresponding to the light receiving surfaces of the light receiving elements 16 may be used. The scintillator-side surface (the top surface in the diagram) of the grid plate-like radio wave shield 26 may be used as a reflecting surface, and the reflector 24 may be omitted. Such a radio wave shield of plate-like shape facilitates a current flow for high shielding performance.

Figure 9:
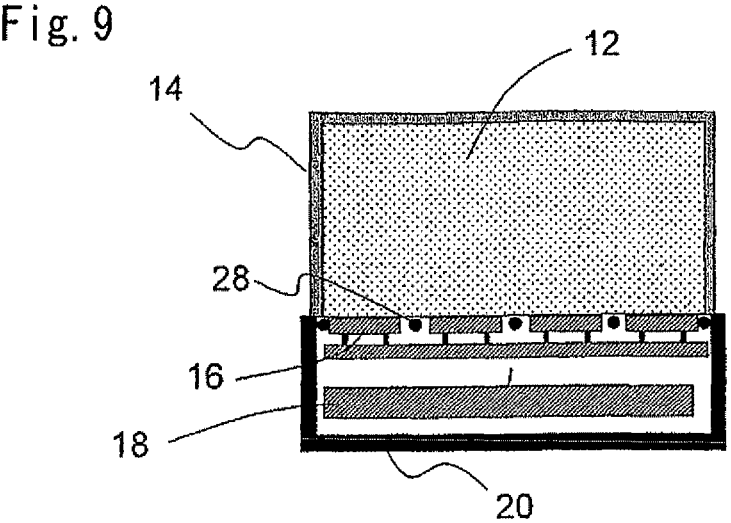
FIG. 9 is a longitudinal cross-sectional view showing the configuration of another modification of the PET detector.
Figure 10:
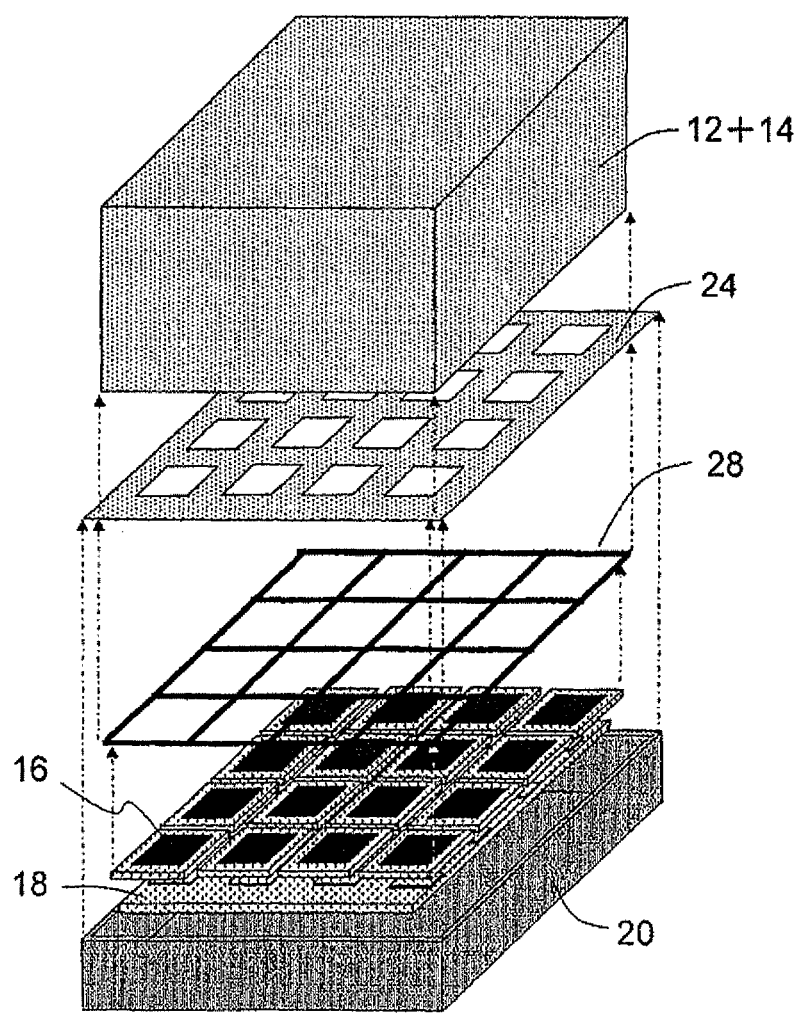
FIG. 10 is an exploded perspective view showing a detailed configuration of the PET detector shown in FIG. 9.

Alternatively, as in another modification shown in FIG. 9 (cross-sectional view) and FIG. 10 (exploded perspective view), a grid line-like radio wave shield 28 may be used which is arranged in gaps between the light receiving elements 16 so as to avoid the light receiving surfaces thereof.

Figure 11:
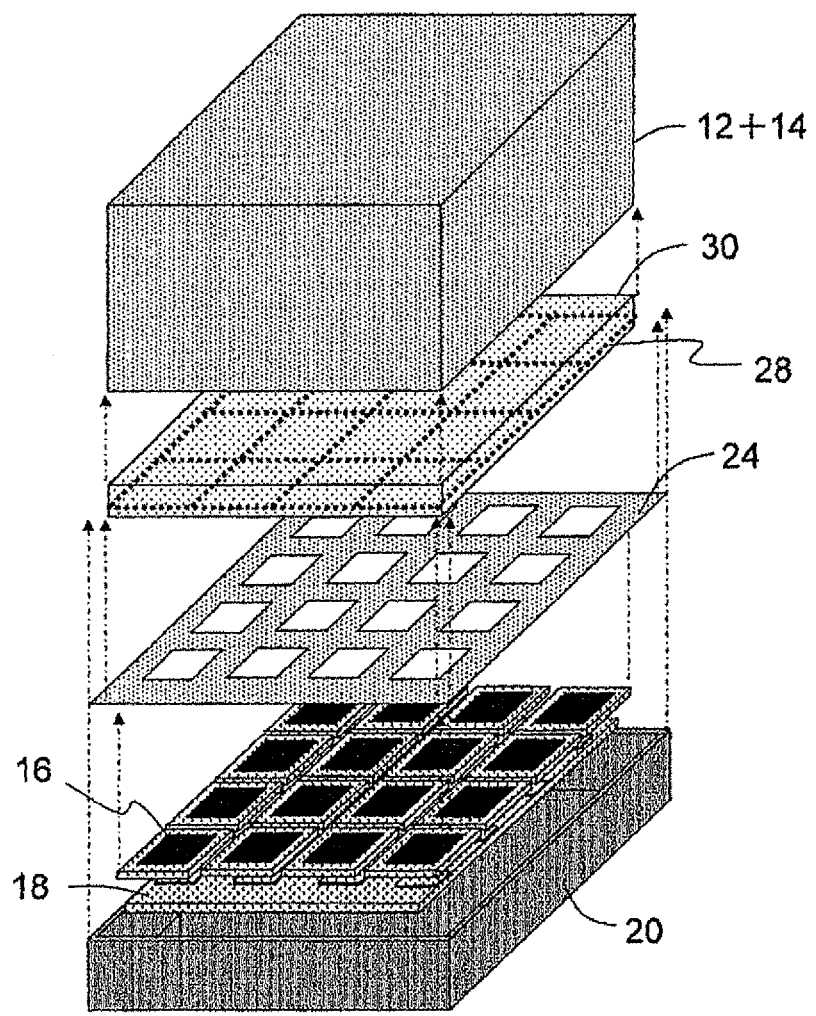
FIG. 11 is an exploded perspective view showing a detailed configuration of yet another modification of the PET detector.

Alternatively, as in yet another modification shown in FIG. 11, a light guide 30 may be inserted between the grid line-like radio wave shield 28 and the scintillator 12 so that the grid line-like radio wave shield 28 is embedded near or in the surface of the light guide 30. The light guide 30 can improve the transmission efficiency of the scintillation light between the scintillator 12 and the light receiving elements 16. If the scintillator 12 and the light receiving elements 16 have different installation areas, the light guide 30 can absorb the difference in the installation area. Examples of the material of the light guide 30 include highly transparent plastics and glass. The embedding (inclusion) of the radio wave shield into the light guide 30 or the attachment to the surface of the light guide 30 can increase the optical continuity between the scintillator 12 and the light receiving elements 16. Note that the radio wave shield of the PET detector for the light guide 30 to be inserted into is not limited to the grid line shape. The wire mesh-like radio wave shield 22 shown in FIG. 5 or the grid plate-like radio wave shield 26 shown in FIG. 8 may be used.

Figure 12:
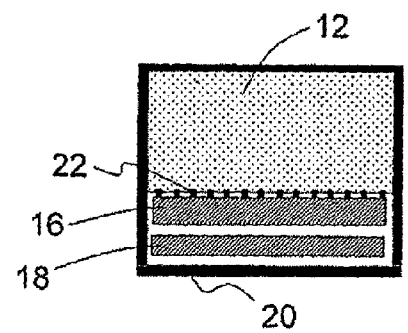
FIG. 12 is a transverse cross-sectional view showing the configuration of yet another modification of the PET detector.

For a simplified structure, as in a modification shown in FIG. 12, the entire PET detector including the scintillator 12 may be covered with a radio wave shield 20. In such a case, the end of the PET detector 10 on the inner side of the measuring port 8P is configured not to protrude from the ends of the coil elements 44 on the inner side of the measuring port 8P.

Figure 13:
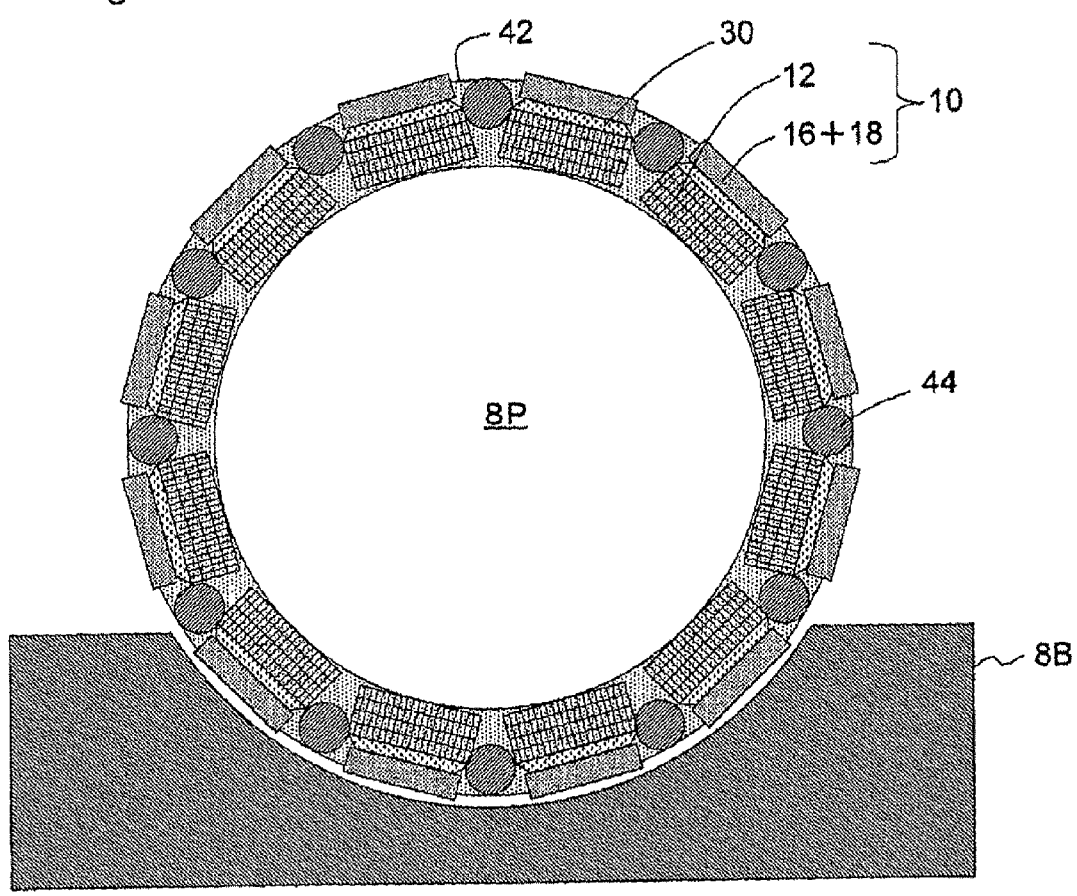
FIG. 13 is a transverse cross-sectional view showing a second embodiment of the integrated PET/MRI scanner including the PET detector shown in FIG. 11.

FIG. 13 shows the configuration of a second embodiment of the integrated PET/MRI scanner according to the present invention, using the PET detector accompanied by a light guide shown in FIG. 11. The light guides 30 are formed in a trapezoidal shape that is larger on the scintillator 12 side, so that scintillators 12 larger than the light receiving areas of the light receiving elements 16 can be connected. The scintillators 12 can also be placed closer to the measuring object as much as the light guides 30 are attached. This can increase the PET sensitivity.

Figure 14:
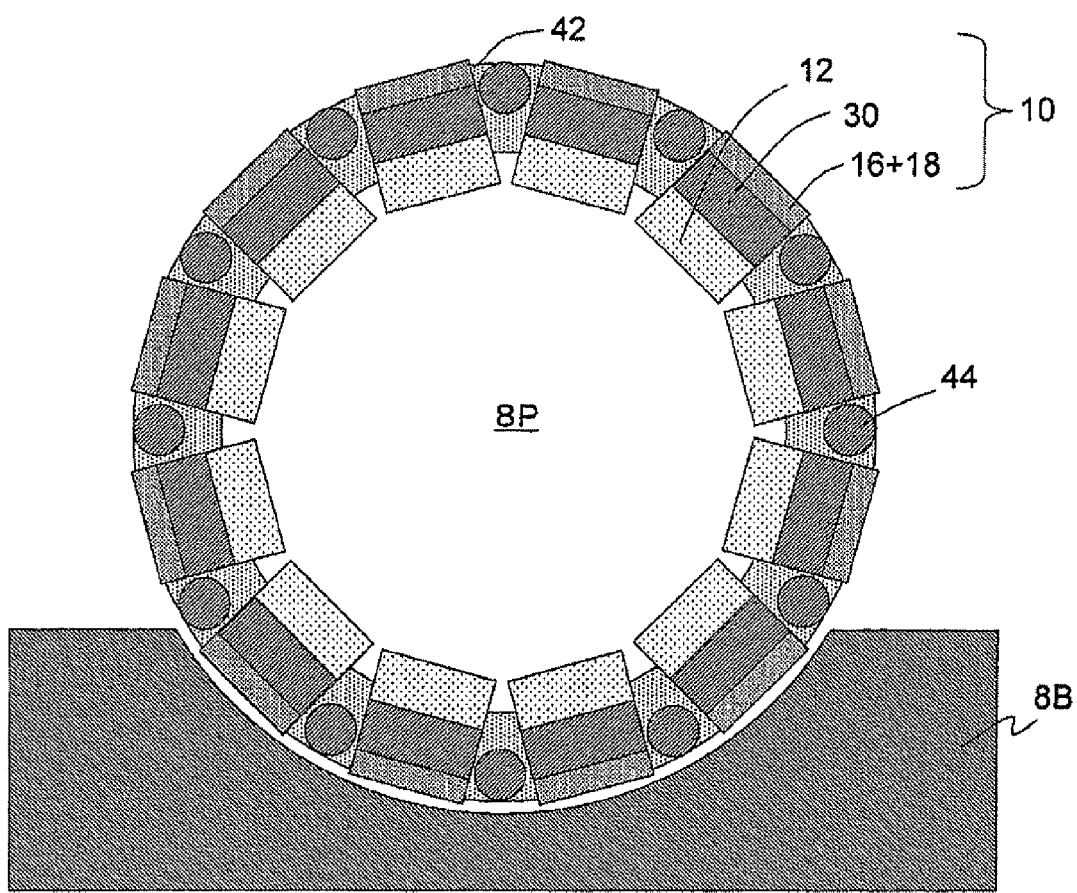
FIG. 14 is a transverse cross-sectional view showing a third embodiment of the integrated PET/MRI scanner according to the present invention.

As in the configuration of a third embodiment shown in FIG. 14, thick light guides 30 can be used to reduce the gaps between the scintillators 12 and place the scintillators 12 closer to the measuring object for increased PET sensitivity, without configuring the light guides 30 into a trapezoidal shape.

Figure 15:
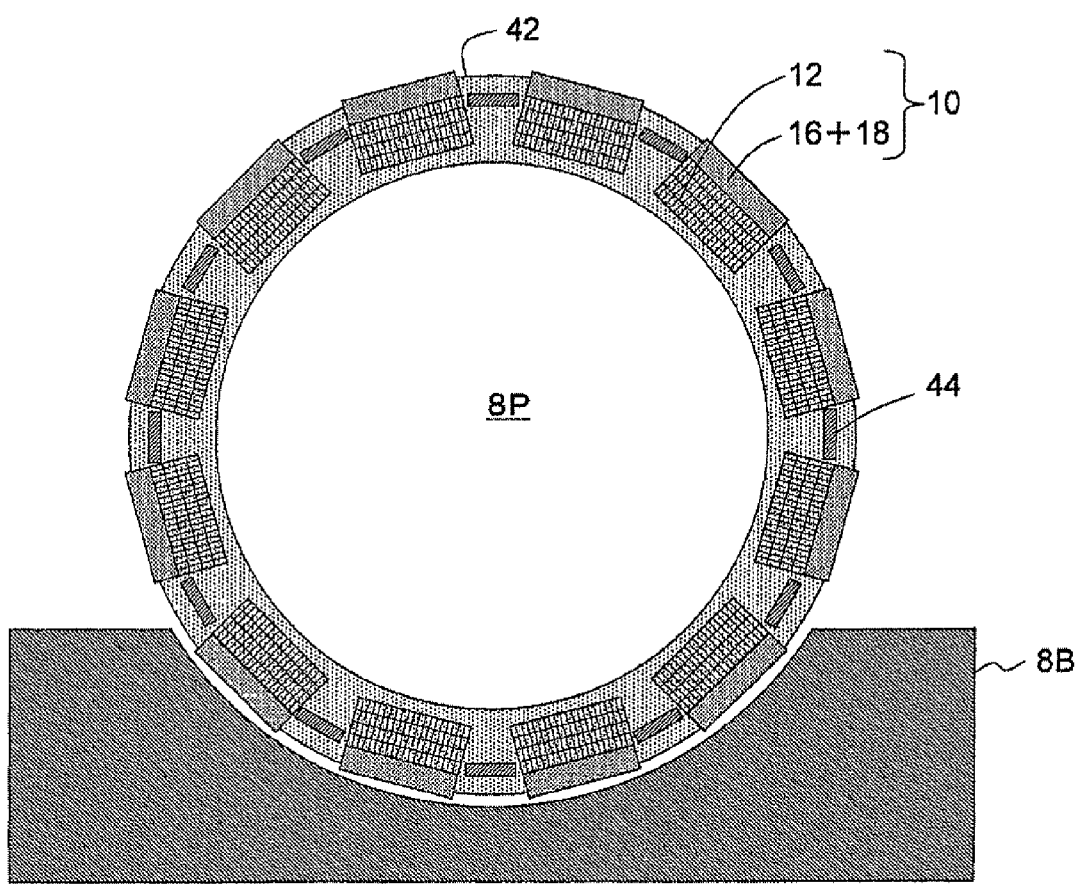
FIG. 15 is a transverse cross-sectional view showing a fourth embodiment of the same.

In any of the foregoing first, second, and third embodiments, the coil elements 44 of the RF col 42 are contained in bar-shaped cases. As in a fourth embodiment shown in FIG. 15, the coil elements 44 may be contained, for example, in plate-shaped cases that are wide in the circumferential direction of the measuring port 8P.

Figure 16:
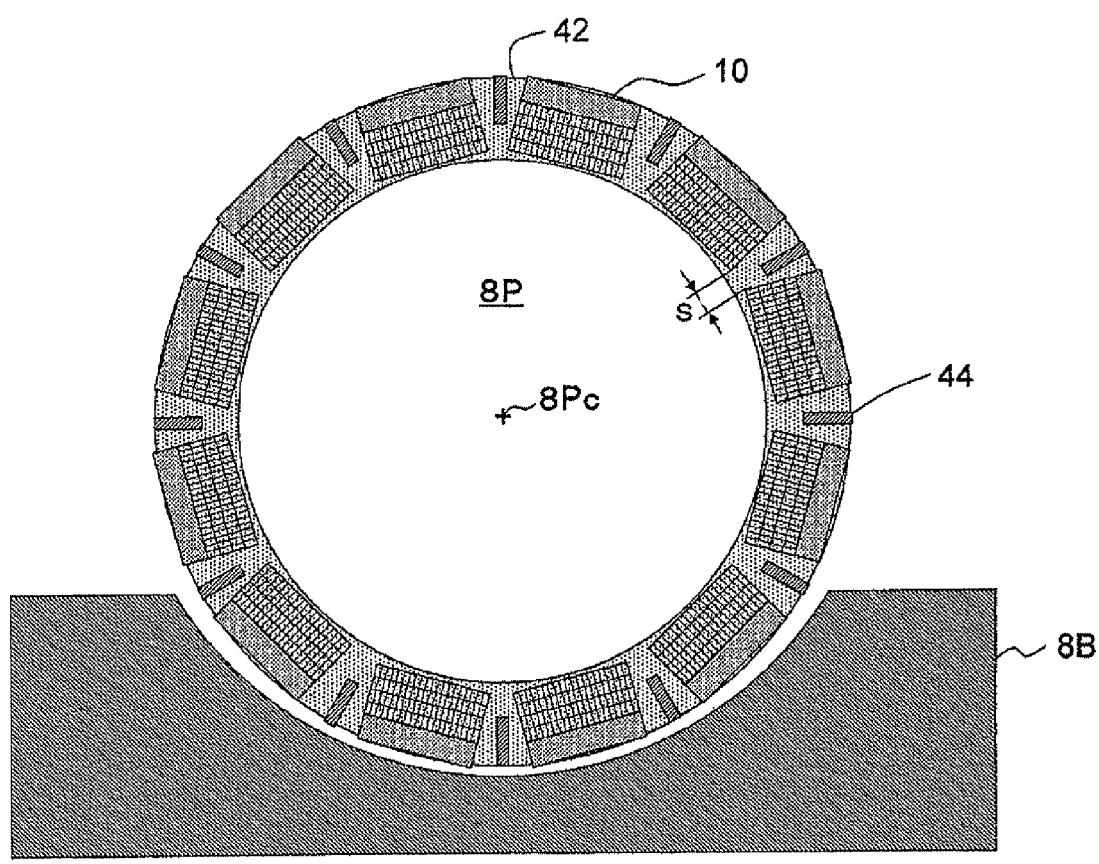
FIG. 16 is a transverse cross-sectional view showing a fifth embodiment of the same.

As in a fifth embodiment shown in FIG. 16, when the plate-shaped coil elements 44 are used, they may be disposed to be wide in radial directions as seen from the center 8Pc of the measuring port. This can reduce the gaps S between the PET detectors 10 to increase the PET sensitivity.

Figure 17:
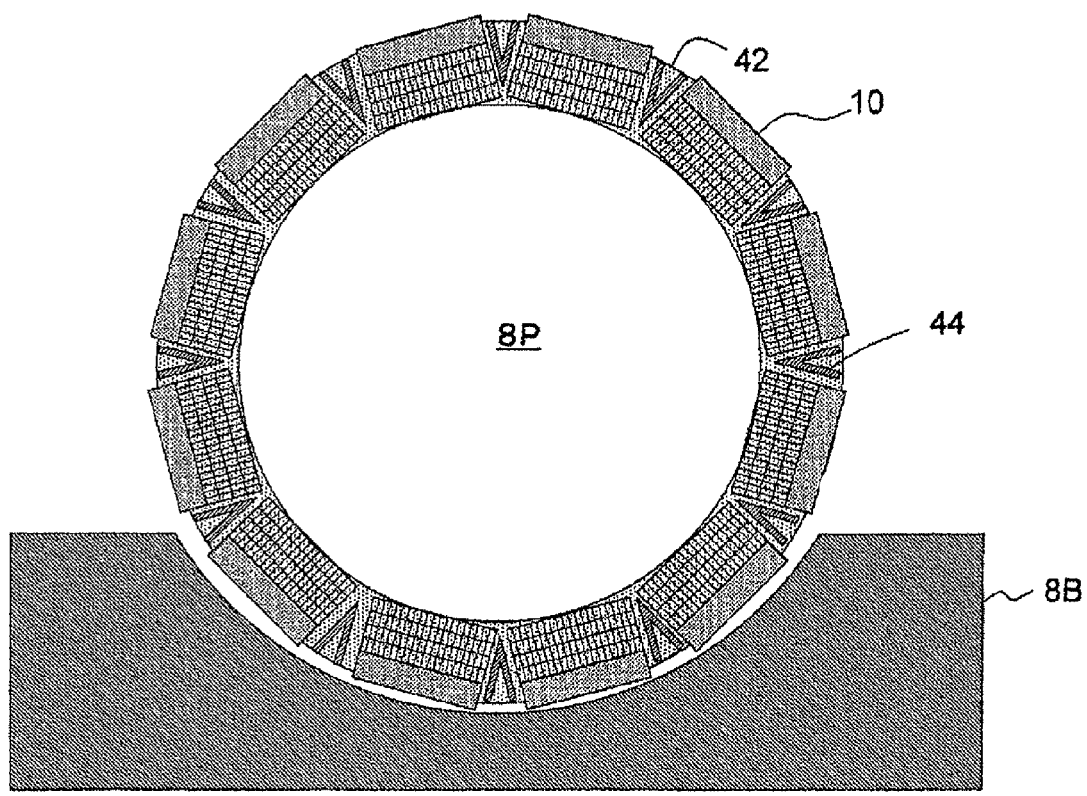
FIG. 17 is a transverse cross-sectional view showing a sixth embodiment of the same.

As in a sixth embodiment shown in FIG. 17, the coil elements 44 of the RF coil 42 may be configured into a V shape according to the spaces between the PET detectors 10. This can increase the arrangement density of the PET detectors, thereby increasing the PET and MRI sensitivities.

Figure 18:
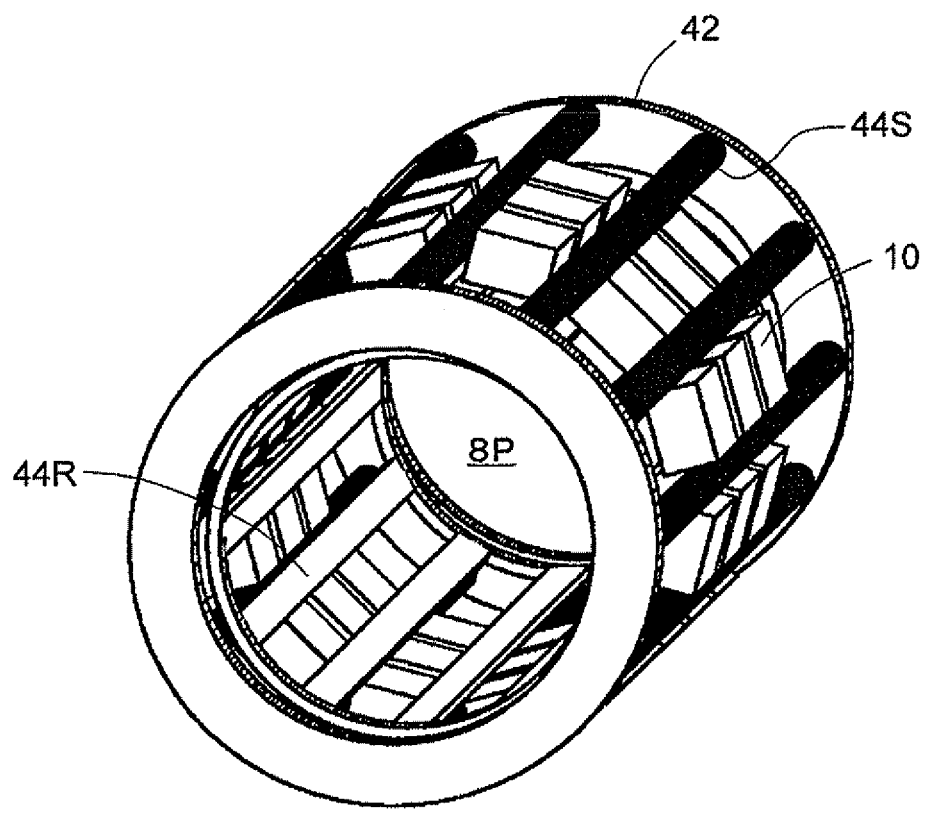
FIG. 18 is a perspective view showing an arrangement of transmitting coil elements, receiving coil elements, and PET detectors used in a seventh embodiment of the PET/MRI scanner according to the present invention.
Figure 19:
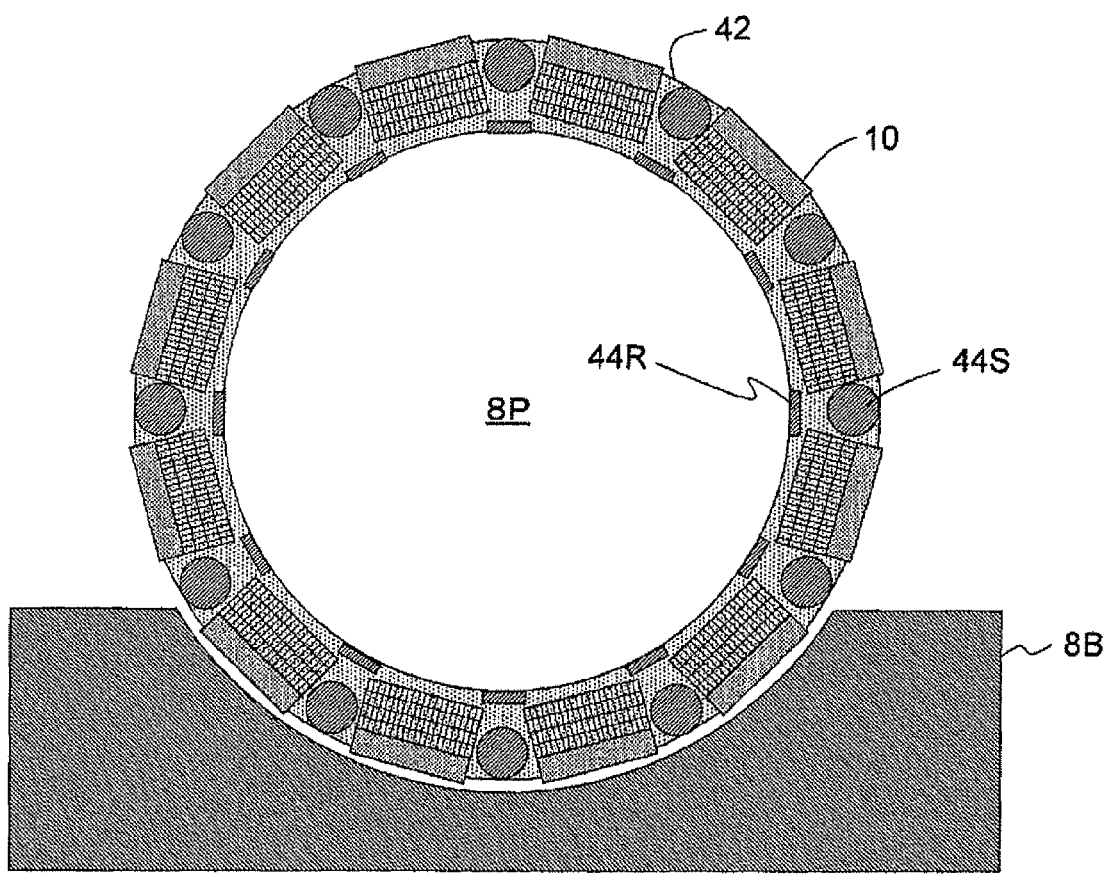
FIG. 19 is a transverse cross-sectional view showing the overall configuration of the same.

In any of the foregoing embodiments, a transmitting and receiving RF coil having transmitting coil elements integrated with receiving coil elements is used as the RF coil. However, as in a seventh embodiment shown in FIG. 18 (a perspective view of essential parts) and FIG. 19 (transverse cross-sectional view), transmitting coil elements 44S and receiving coil elements 44R of the RF coil 42 may be separated. The transmitting coil elements 44S are contained in bar-shaped cases, for example. The receiving coil elements 44R are contained in plate-shaped cases wider in the circumferential direction of the measuring port 8P, for example. Only the transmitting coil elements 44S may be arranged between the PET detectors 10. Since the coil elements have only a small absorption effect on 511-keV radiations which are measured in PET, the receiving coil elements 44R can be thus placed in front of the PET detectors 10.

In the present embodiment, at least the ends of the receiving coil elements 44R on the inner side of the measuring port 8P are located further in the measuring port 8P than the ends of the PET detectors 10 on the inner side of the measuring port 8P. The PET detectors 10 therefore will not interfere with the MRI reception sensitivity. Consequently, even if the scintillator portions of the PET detectors 10 include radio wave shields, their effect can be reduced. If the scintillator portions thus include radio wave shields, the ends of the transmitting coil elements 44S of the RF coil 42 on the inner side of the measuring port 8P are preferably located further in the measuring portion 8P than the ends of the radio wave shields on the inner side of the measuring port 8P. As a result, the scintillators 12 can be placed close to the measuring object for improved sensitivity.

Figure 20:
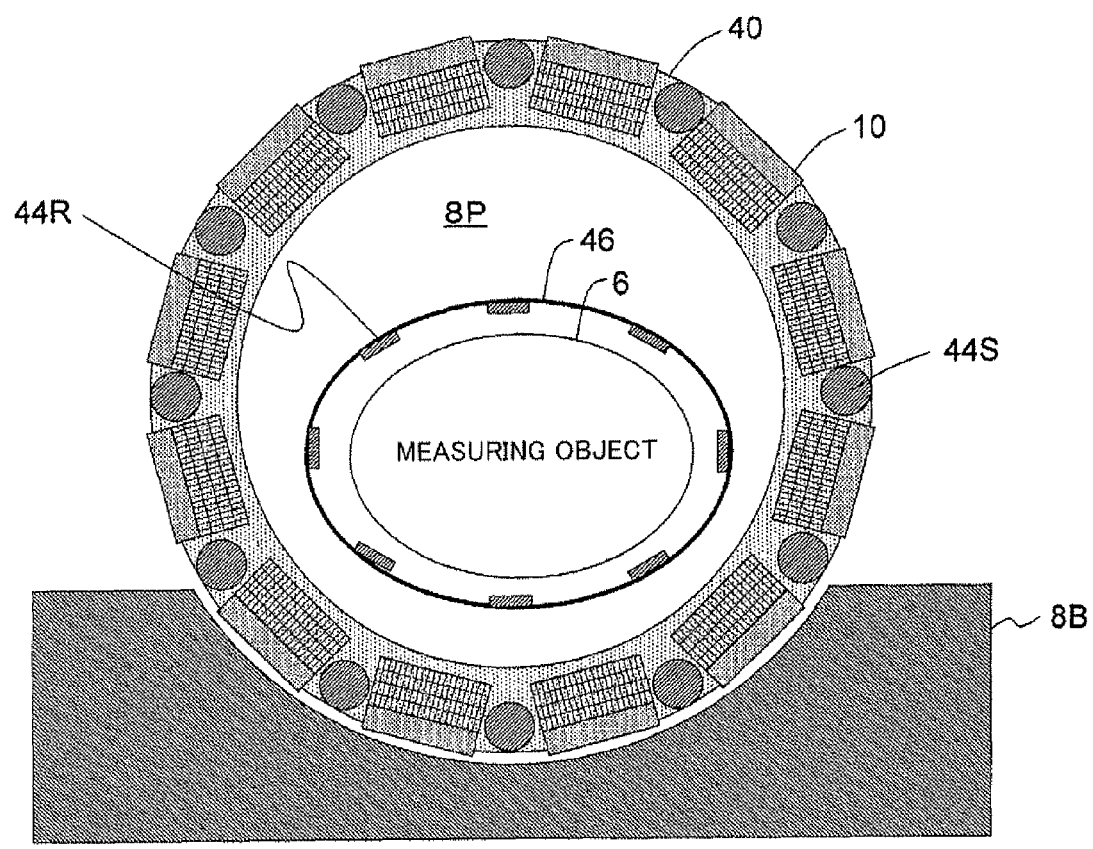
FIG. 20 is a transverse cross-sectional view showing an eighth embodiment of the PET/MRI scanner according to the present invention.

The receiving coil elements 44R need not necessarily be fixed to a frame of the RF coil 42 as in the seventh embodiment. As in an eighth embodiment shown in FIG. 20, the receiving coil elements 44R may be arranged on a flexible coil holding band 46 and wound around the measuring object 6 for a further improvement in the MRI sensitivity.

Figure 21:
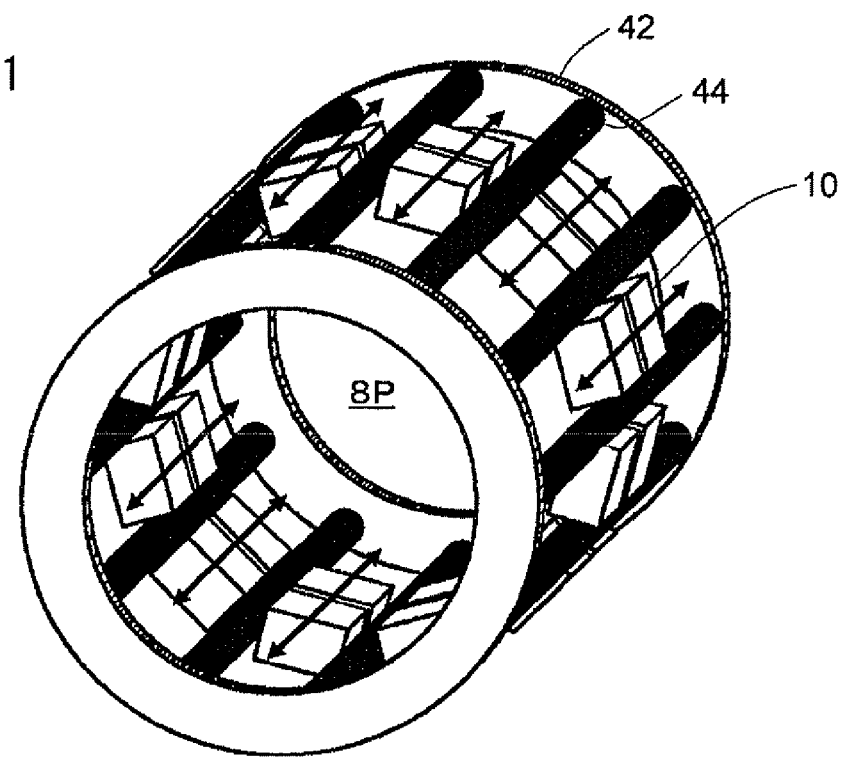
FIG. 21 is a perspective view showing the configuration of essential parts of a ninth embodiment of the same.

The PET detectors 10 need not be fixed to the frame of the RF col 42, either. As in a ninth embodiment shown in FIG. 21, the PET detectors 10 may be configured to be slidable in the frame of RF coil 42, so that the PET detectors 10 can be moved in the axial direction of the measuring port 8P and adjusted to required resolution of the measuring object etc.

Figure 22:
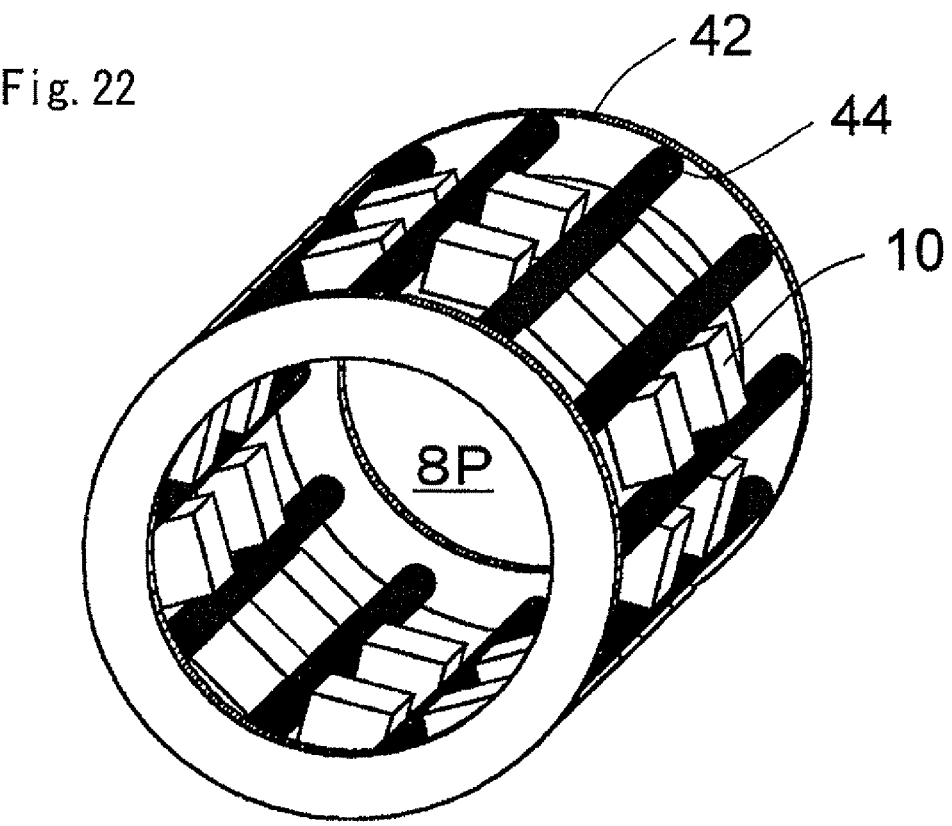
FIG. 22 is a perspective view showing the configuration of essential parts of a tenth embodiment of the same.
Figure 23:
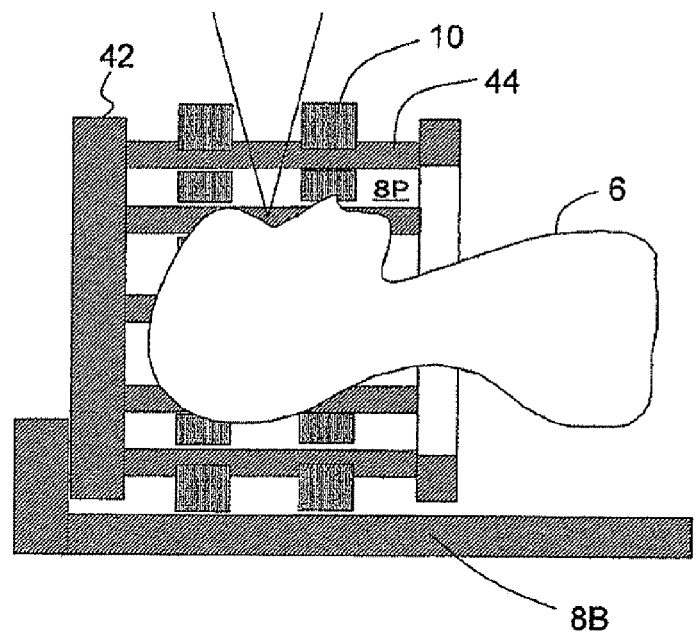
FIG. 23 is a longitudinal cross-sectional view of the same.

For example, as in a tenth embodiment shown in FIG. 22 (a perspective view of essential parts) and FIG. 23 (a transverse cross-sectional view showing a measuring state), the PET detectors 10 may be spaced wide at a portion corresponding to, for example, the eyes of the measuring object 6 so as to not block the view of the measuring object 6 and eliminate anxiety during measurement.

In any of the foregoing embodiments, the present invention is applied to a head RF coil of the MRI scanner, and the PET detectors 10 are arranged coaxially to the axis of the measuring port 8P of the MRI scanner 8. The present invention is not limited to such applications, and may be applied to other than the head.

Figure 24:
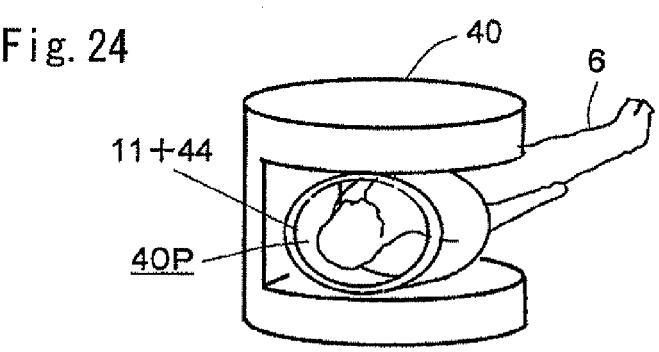
FIG. 24 is a perspective view showing the overall configuration of an eleventh embodiment of the PET/MRI scanner according to the present invention.
Figure 25:
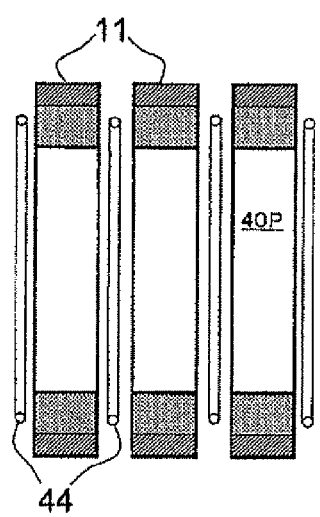
FIG. 25 is a longitudinal cross-sectional view showing the relationship between PET detector rings and an RF coil according to a twelfth embodiment.

For example, as in an eleventh embodiment shown in FIG. 24 (perspective view) and FIG. 25 (a longitudinal sectional view of ring portions), two ring-like arrangements of PET detectors 10, or rings 11 (referred to as PET detector rings), may be disposed with a space therebetween for a vertical static magnetic field (static magnetic field perpendicular to the body axis) of an MRI scanner 40 of so-called hamburger shape. Multi-ring coil elements 44 may be interposed between the two PET detector rings 11. In the diagram, 40P represents a measuring port.

Figure 26:
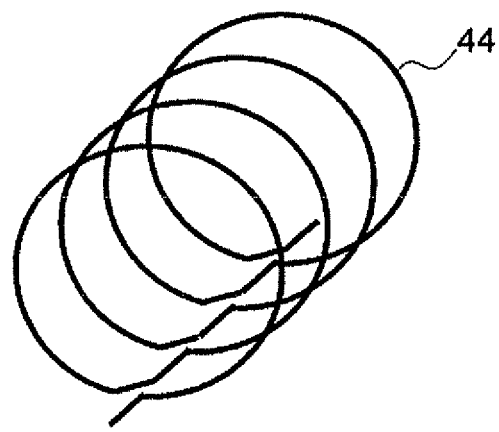
FIG. 26 is a perspective view showing a state of connection of the RF coil of the same.
Figure 27:
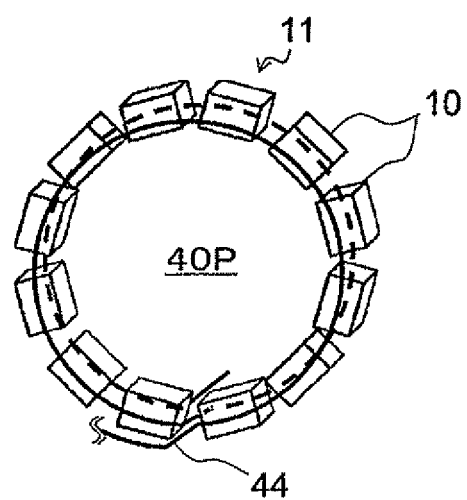
FIG. 27 is a perspective view showing an arrangement of the RF coil and PET detectors in each PET detector ring of the same.

FIG. 26 shows a state of connection of the coil elements 44. FIG. 27 shows a state where PET detectors 10 of each PET detector ring 11 are inserted between the coil elements 44.

In any of the foregoing embodiments, neither the RF coil nor the PET detector rings are limited to a circular configuration.

INDUSTRIAL APPLICABILITY

An integrated PET/MRI scanner can be provided in which PET detectors can be placed close to a measuring object to increase the sensitivity and spatial resolution of PET.

REFERENCE SIGNS LIST

6 . . . measuring object
8, 40 . . . MRI scanner
8P, 40P . . . measurement port
10 . . . PET detector
11 . . . PET detector ring
12 . . . scintillator
14 . . . light shielding member
16 . . . light receiving element
18 . . . front end circuit
20 . . . radio wave shield
22 . . . wire mesh-like radio wave shield
24 . . . reflector
26 . . . grid plate-like radio wave shield
28 . . . grid line-like radio wave shield
30 . . . light guide
42 . . . RF coil
44 . . . coil element
44S . . . transmitting coil element
44R . . . receiving coil element
46 . . . coil holding band

The invention claimed is:

1. An integrated PET/MRI scanner comprising an RF coil for MRI and a plurality of PET detectors in a measuring port of an MRI scanner, wherein
the RF coil for MRI is divided into a transmitting coil element and a receiving coil element,
the PET detectors are disposed with spaces therebetween and the transmitting coil element of the RF coil for MRI is disposed between adjacent PET detectors,
wherein, with respect to the measuring port, a radially-inner most end of the receiving coil element of the RF coil for MRI is located further radially inward than a radially-inner most end of the PET detectors,
each PET detector includes a combination of a scintillator that senses radiation and emits light and a light receiving element that senses the light emitted from the scintillator and converts the sensed light into an electrical signal, and
wherein, with respect to the measuring port, a radially inner-most end of the scintillator of each PET detector is located further radially inward than a radially inner-most end of the transmitting coil element.

2. An integrated PET/MRI scanner comprising an RF coil for MRI and a plurality of PET detectors in a measuring port of an MRI scanner, wherein
the PET detectors are disposed with spaces therebetween and at least a coil element of the RF coil for MRI is disposed between adjacent PET detectors,
each PET detector includes a radio wave shield, and with respect to the measuring port, a radially inner-most end of the coil element is located further radially inward than a radially inner-most end of the radio wave shield,
each PET detector further includes a combination of a scintillator that senses radiation and emits light and a light receiving element that senses the light emitted from the scintillator and converts the sensed light into an electrical signal, and with respect to the measuring port, the scintillator is disposed further radially inward than the light receiving element,
wherein the radio wave shield of each PET detector is disposed on non-light-receiving sides of the light receiving element rather than on the scintillator such that an outer periphery of the scintillator has no radio wave shield to cover the scintillator, and
with respect to the measuring port, a radially inner-most end of the scintillator of each PET detector is disposed further radially inward than the radially inner-most end of the coil element.

3. The integrated PET/MRI scanner according to claim 2, wherein
the RF coil for MRI includes a transmitting coil and the coil element is a transmitting coil element.

4. The integrated PET/MRI scanner according to claim 2, wherein
each PET detector further includes a second radio wave shield disposed between the scintillator and the light receiving element.

5. The integrated PET/MRI scanner according to claim 2, wherein
each PET detector further includes a front end circuit, and wherein the radio wave shield of each PET detector is disposed so as to shield substantially only the light receiving element and the front end circuit.

* * * * *

UNITED STATES PATENT AND TRADEMARK OFFICE
CERTIFICATE OF CORRECTION

PATENT NO.        : 9,510,797 B2
APPLICATION NO.   : 13/880842
DATED             : December 6, 2016
INVENTOR(S)       : Taiga Yamaya et al.

It is certified that error appears in the above-identified patent and that said Letters Patent is hereby corrected as shown below:

On the Title Page

Item (73) should read:
Assignee: NATIONAL INSTITUTES FOR QUANTUM AND RADIOLOGICAL SCIENCE AND TECHNOLOGY Signed and Sealed this
Twenty-eighth Day of August, 2018

Andrei Iancu
*Director of the United States Patent and Trademark Office*